United States Patent [19]

Takago et al.

[11] Patent Number: 4,497,943

[45] Date of Patent: Feb. 5, 1985

[54] ORGANOCYCLOPOLYSILOXANE AND A ROOM TEMPERATURE CURABLE COMPOSITION CONTAINING SAME

[75] Inventors: Toshio Takago; Osamu Sodeyama; Masami Terashima, all of Gunma, Japan

[73] Assignee: Shin-Etsu Chemical Co., Ltd., Tokyo, Japan

[21] Appl. No.: 487,203

[22] Filed: Apr. 21, 1983

[30] Foreign Application Priority Data

Apr. 26, 1982 [JP] Japan ................................. 57-69838

[51] Int. Cl.$^3$ .............................................. C08G 77/06
[52] U.S. Cl. ...................................... 528/22; 524/780; 524/783; 524/785; 524/789; 524/860; 524/865; 528/33; 556/450; 556/453; 556/460; 556/456
[58] Field of Search .............. 556/460, 450, 453, 456; 528/22, 33; 524/865, 780, 785, 783, 789, 860

[56] References Cited

U.S. PATENT DOCUMENTS

| | | | |
|---|---|---|---|
| 2,849,473 | 8/1958 | Bailey et al. ........................ | 556/460 |
| 4,248,993 | 2/1981 | Takago ................................ | 528/32 |
| 4,374,950 | 2/1983 | Shimizu .............................. | 528/33 |

FOREIGN PATENT DOCUMENTS 1249276  9/1967  Fed. Rep. of Germany .

*Primary Examiner*—Melvyn I. Marquis
*Attorney, Agent, or Firm*—Toren, McGeady and Stanger

[57] ABSTRACT

The room temperature curable organopolysiloxane composition of the invention comprises a dimethylpolysiloxane terminated at both molecular chain ends with silanolic hydroxy groups, an organocyclopolysiloxane, typically a cyclotetrasiloxane, having 2 or more alkenyloxy groups such as isopropenyloxy groups in a molecule as a crosslinking agent for the dimethylpolysiloxane and a guanidyl-containing organosilane or polysiloxane compound as a curing catalyst. The composition is capable of giving a cured rubbery elastomer when kept in a moisture-containing atmosphere at room temperature without the problems in the prior art compositions such as noxious condensation products or poor adhesion to the surface of the substrate on which the composition has been cured. The above mentioned organocyclopolysiloxane having alkenyloxy groups along with one or more of trihydrocarbylsiloxy groups or, typically, trimethylsiloxy groups bonded to the silicon atoms in the ring structure is a novel compound not described in any prior art literatures.

17 Claims, 2 Drawing Figures

ORGANOCYCLOPOLYSILOXANE AND A ROOM TEMPERATURE CURABLE COMPOSITION CONTAINING SAME

BACKGROUND OF THE INVENTION

The present invention relates to a novel organocyclotetrasiloxane and a room temperature curable composition containing the same.

There are known several types of room temperature curable silicone rubber compositions capable of giving a rubbery elastomer when kept standing under atmospheric condition. They are classified according to the storability of the ready-mixed composition into so-called two-package type ones and one-package type ones, the composition of the former type being stored in two separate packages each containing different ingredient or ingredients from the other to be blended together directly before application and the composition of the latter type being storable in one package containing all of the ingredients of the composition blended together in advance.

The room temperature curable silicone rubber compositions are also classified into several types according to the mechanism of the crosslinking reaction by which the composition is cured. Most of the crosslinking reactions proceed by the mechanism of condensation reaction between functional groups and the condensation products produced by the reaction may be an amine, a hydroxylamine, an oxime, a carboxylic acid, e.g. acetic acid, or an alcohol. The condensation products other than the alcohols are all toxic or corrosive so that application of the silicone rubber compositions curable with formation of such noxious condensation products is greatly limited unless good ventilation is provided in the working place. On the other hand, the room temperature curable silicone rubber compositions curable by the dealcoholation condensation are free from the problem of noxious gaseous condensation products produced by the crosslinking reaction although the compositions of this type have other disadvantages of poor storability of the ready mixed composition, relatively long curing time and brittleness or fragility of the cured product.

Furthermore, the curing catalysts and the curing accelerators formulated in these room temperature curable silicone rubber compositions also cause some problems. For example, titanium alkoxide compounds as a curing accelerator and certain metal salts of carboxylic acids used as a curing catalyst in the compositions curable by producing acetic acid or an oxime as the condensation product remain in the cured product and cause coloration and decrease in the mechanical properties thereof in addition to the problem of toxicity in some cases.

Accordingly, there have been recently developed improved room temperature curable silicone rubber compositions in which the crosslinking reaction proceeds by the condensation reaction with formation of a ketone compound as the condensation product when the composition is kept in a moisture-containing atmosphere (see, for example, Japanese Patent Publications Nos. 51-39274, 51-39673 and 54-44699). The compositions of this type have no problems in respect of the corrosiveness and adhesion to the substrate surface but they are disadvantageous due to the not always satisfactory ultimate elongation of the cured rubbery elastomer.

SUMMARY OF THE INVENTION

It is therefore an object of the present invention to provide a novel and improved room temperature curable silicone rubber composition freed from the above described problems and disadvantages in the prior art compositions.

Another object of the present invention is to provide a novel organocyclotetrasiloxane which is not described in any prior art literatures and is useful as a crosslinking agent in the above mentioned room temperature curable silicone rubber composition as combined with a diorganopolysiloxane as the main ingredient thereof.

Thus, the room temperature curable silicone rubber composition of the present invention comprises:

(a) 100 parts by weight of a diorganopolysiloxane terminated at both molecular chain ends with silanolic hydroxy groups;

(b) from 0.01 to 25 parts by weight of a polyfunctional organocyclopolysiloxane represented by the general formula

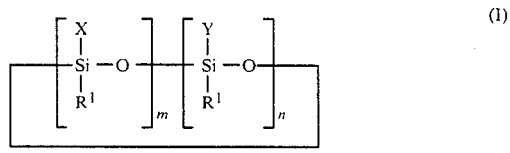
(I)

in which X is an alkenyloxy group expressed by the formula $-OCR^3=CH-R^2$, Y is a trihydrocarbylsiloxy group of the formula $-O-SiR^1_3$ or a monovalent hydrocarbon group having from 1 to 5 carbon atoms, $R^1$ is a monovalent hydrocarbon group having from 1 to 8 carbon atoms, $R^2$ and $R^3$ are each independently a hydrogen atom or a substituted or unsubstituted monovalent hydrocarbon group having from 1 to 6 carbon atoms, m is a positive integer of 2, 3 or 4 and n is zero or a positive integer with the proviso that m+n is 4, 5 or 6; and (c) from 0.01 to 5 parts by weight of an organosilane or an organopolysiloxane having, in a molecule, at least one substituted or unsubstituted guanidyl group of the formula $$(R^4_2N-)_2C=N- \qquad (II)$$

in which each $R^4$ is a hydrogen atom or a monovalent hydrocarbon group independently from the others.

The above described organocyclopolysiloxane of the formula (I) is a novel compound not described in any prior art literatures. In particular, an organocyclotetrasiloxane of the formula

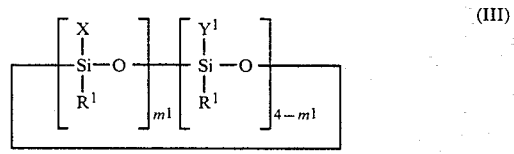
(III)

in which X and $R^1$ each have the same meaning as defined above, $Y^1$ is a trimethylsiloxy group of the formula —O—Si(CH$_3$)$_3$ and m$^1$ is 2 or 3, is useful as the component (b) in the inventive composition.

DETAILED DESCRIPTION OF THE PREFERRED EMBODIMENTS

Figure 1:
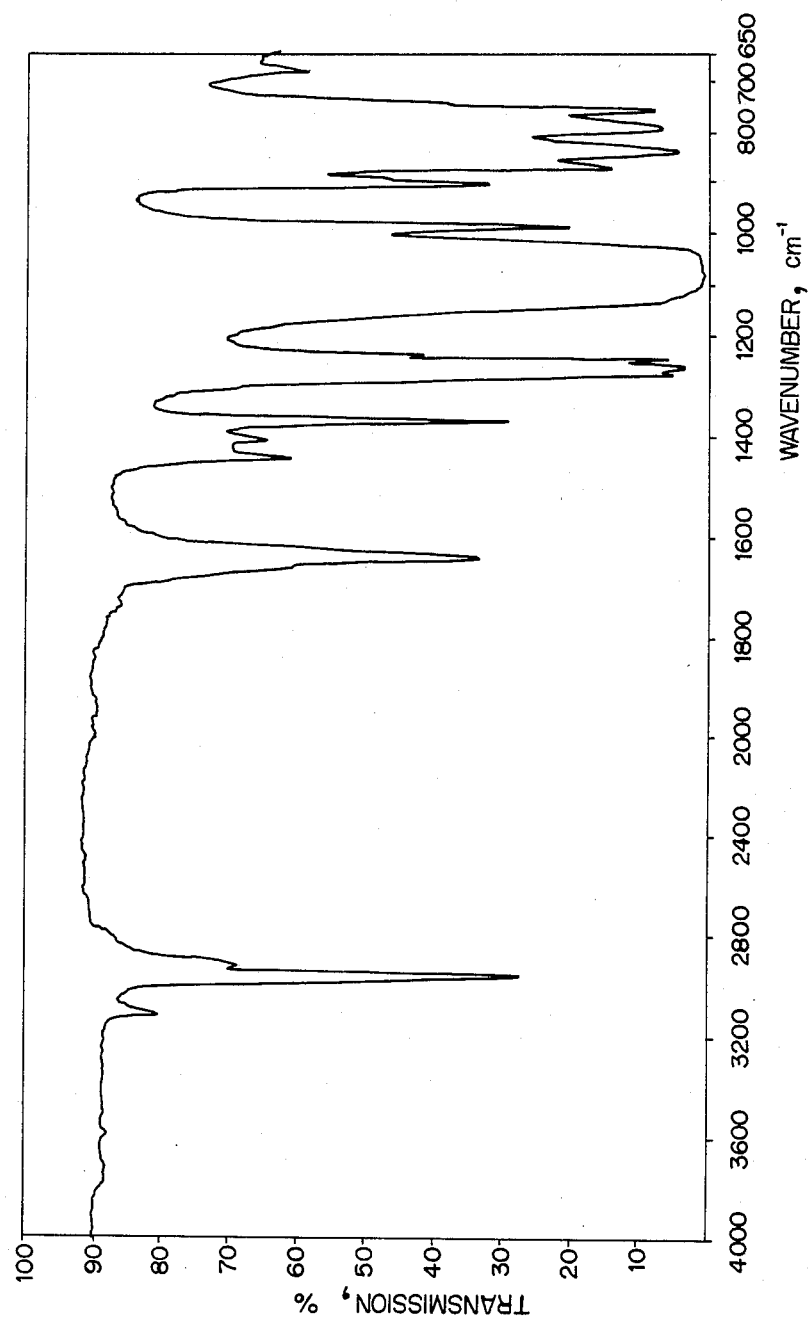
FIGS. 1 and 2 are each an infrared absorption spectrum of one of the organocyclotetrasiloxanes of the formula (III) synthesized in Example 1 given below.

The above described formulation of the inventive composition has been established as a result of the extensive investigations undertaken by the inventors to seek a novel crosslinking agent leading to the discovery that the composition essentially composed of the above three components (a) to (c) is very stable and storable over a long period of time under a hermetically sealed condition, that the composition is rapidly cured when kept under the atmospheric condition containing moisture without producing any noxious gaseous product having toxicity or corrosiveness, that the cured product thereof is a rubbery elastomer with low elastic modulus and large elongation, that the composition cured on a substrate surface exhibits strong adhesion to the surface without corrosiveness and that, when the composition is used as a sealant or a caulking material, the surface of the cured composition as well as the surfaces of the parts adjacent thereto are remarkably free from surface stain as is sometimes a serious problem in the use of a conventional silicone sealant composition.

Following is a description of each of the essential components in the room temperature curable silicone rubber composition of the present invention.

In the first place, the base component, i.e. the component (a), in the inventive composition is a diorganopolysiloxane having a substantially linear molecular structure as represented by an average unit formula $R_aSiO_{4-a/2}$, in which R is a substituted or unsubstituted monovalent hydrocarbon group and a is a positive number in the range from 1.90 to 2.05, and terminated at both molecular chain ends with silanolic hydroxy groups. The group denoted by the symbol R is exemplified by the monovalent hydrocarbon groups including alkyl groups such as methyl, ethyl, propyl, isopropyl, butyl, 2-ethylbutyl and octyl groups, cycloalkyl groups such as cyclohexyl and cyclopentyl groups, alkenyl groups such as vinyl, allyl and hexenyl groups, aryl groups such as phenyl, tolyl, xylyl, biphenyl and phenonetolyl groups and aralkyl groups such as benzyl and phenylethyl groups and substituted hydrocarbon groups obtained by replacing part or all of the hydrogen atoms in the above named hydrocarbon groups with substituent atoms or groups, e.g. halogen atoms and cyano groups, including halogenated hydrocarbon groups such as chloromethyl, trichloropropyl, bromophenyl and chlorocyclohexyl groups and cyano-substituted hydrocarbon groups such as 2-cyanoethyl, 3-cyanopropyl, 4-cyanobutyl and 2-cyanobutyl groups.

It is preferable that the diorganopolysiloxane as the component (a) in the inventive composition should have a viscosity of at least 25 centistokes at 25° C. in order that the cured product obtained by curing the composition may have excellent mechanical strengths.

The alkenyloxy-containing polyfunctional organocyclopolysiloxane as the component (b) is represented by the above given general formula (I). Typical examples of the alkenyloxy group denoted by the symbol X are isopropenyloxy, 1-isobutynyloxy, 1-methyl-1-propenyloxy, 1,4-dimethyl-1,3-pentadienyloxy and cyclohexenyloxy groups. Further, the group denoted by the symbol Y may be a trimethylsiloxy or triethylsiloxy group as the examples of the trihydrocarbylsiloxy groups and an alkyl group, e.g. methyl, ethyl, propyl and butyl groups, or an alkenyl group, e.g. vinyl and allyl groups, as the examples of the monovalent hydrocarbon group having from 1 to 5 carbon atoms. The group denoted by the symbol R$^1$ is a monovalent hydrocarbon group having from 1 to 8 carbon atoms or, preferably, a methyl group.

The formulas (i) to (xii) given below are several of the examples of the organocyclopolysiloxanes suitable as the component (b) in the inventive composition, in which Me and Pr denote each a methyl group and a propyl group, respectively, and X is either one of the alkenyloxy groups named above.

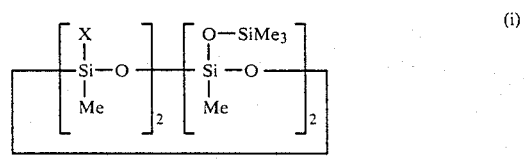
(i)

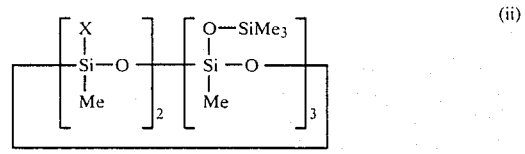
(ii)

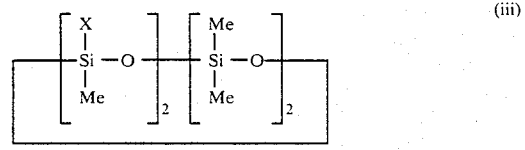
(iii)

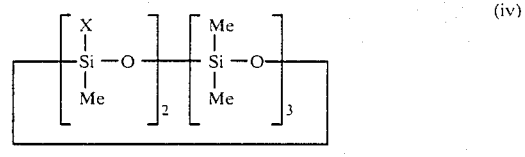
(iv)

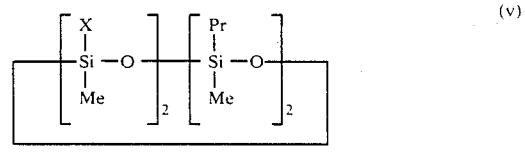
(v)

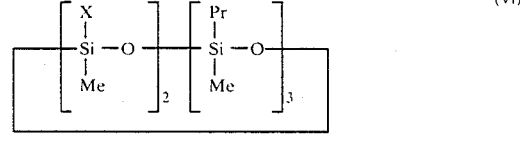
(vi)

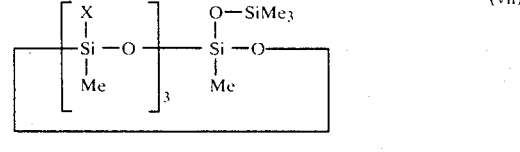
(vii)

-continued

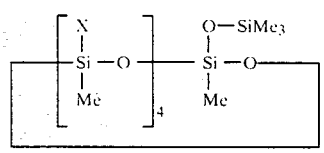
(viii)

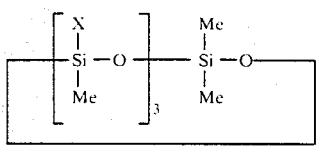
(ix)

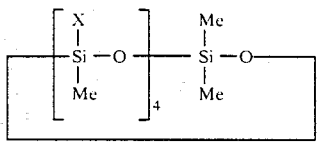
(x)

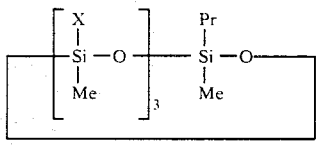
(xi)

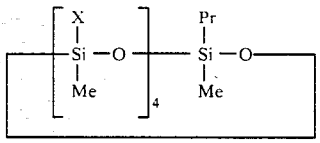
(xii)

The amount of this component (b) in the inventive composition should be in the range from 0.01 to 25 parts by weight or, preferably, from 0.1 to 20 parts by weight per 100 parts by weight of the component (a). This is because no satisfactory curing can be obtained when the amount of this component (b) is too small while an excessively large amount of the component (b) is undesirable due to the decreased elasticity of the cured product as well as increased shrinkage of the composition in the course of curing.

When a relatively low elastic modulus and large elongation are desired in the cured product of the composition, it is preferable that the component (b) is a combination of two different types of the organocyclopolysiloxanes of the formula (I), one having the values of m and n in the formula equal to 2 and 2 or 3, respectively, and the other having the value of m equal to 3 or larger. The molar ratio of the cyclopolysiloxane of the former type to the latter type is preferably in the range from 99.5:0.5 to 70:30.

As is mentioned before, the organocyclopolysiloxanes used in the inventive composition as the component (b) are novel compounds not described in any prior art literatures so that the procedures for the preparation thereof is described below in some detail taking the compounds expressed by the above given formulas (i) and (vii) as the examples. The starting compound for the synthesis of these compounds is 1,3,5,7-tetramethyl cyclotetrasiloxane and the synthetic route therefrom is as follows.

(A) A mixture composed of 1 mole of the above given tetramethyl cyclotetrasiloxane and 1.8 moles of trimethyl silanol is subjected to a dehydrogenation condensation reaction in the presence of about 0.025 mole of diethyl hydroxylamine as a catalyst so that the reaction product is a mixture of two kinds of trimethylsiloxy-containing cyclotetrasiloxanes expressed by the following formulas:

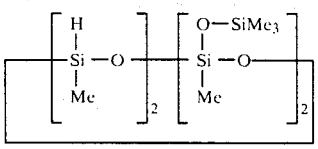
(xiii)

and

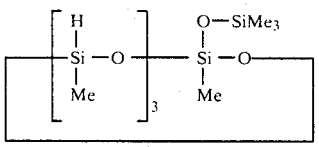
(xiv)

(B) The reaction product obtained in the step (A) above is dissolved in carbon tetrachloride and reacted with chlorine to effect dehydrochlorination reaction so that the hydrogen atoms directly bonded to the silicon atoms in the cyclic polysiloxanes are replaced with chlorine atoms to form two kinds of the chlorine-containing cyclotetrasiloxanes expressed by the following formulas:

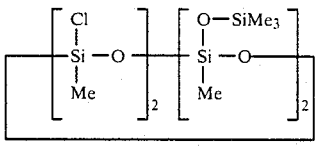
(xv)

and

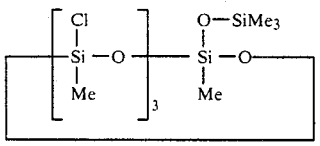
(xvi)

(C-1) One mole of the above given chlorine-containing cyclic polysiloxane of the formula (xv) is mixed with 27 moles of acetone, 2.6 moles of triethylamine, dimethyl formamide in an amount of 20% by weight based on the acetone taken above and 2 g of copper (I) chloride as a catalyst and the reaction mixture is heated under reflux at about 60° C. for 10 hours to form the cyclotetrasiloxane of the formula (i) in which the group X is an isopropenyloxy group.

(C-2) The chlorine-containing cyclic polysiloxane of the formula (xvi) above can also be converted to the compound of the formula (vii) by introducing the isopropenyloxy groups as the group denoted by X in just the same manner as in the step (C-1) above. In this case, the amount of the triethylamine should be increased to 3.9 moles per mole of the chlorine-containing cyclic polysiloxane of the formula (xvi).

The third of the essential components in the inventive composition, i.e. component (c), is an organosilane or organopolysiloxane compound having at least one substituted or unsubstituted guanidyl group expressed by the formula (II) in a molecule. The symbol $R^4$ in the formula denotes a hydrogen atom or a monovalent hydrocarbon group which is preferably a methyl group so that the group of the formula (II) is a tetramethyl guanidyl group. The manner in which the guanidyl group is bonded to the silicon atom is not particularly limitative and it may be bonded to a silicon atom preferably through an alkylene group, e.g. trimethylene group. This compound serves as a crosslinking promotor between the components (a) and (b).

Following are the formulas of several of the suitable organosilane and organopolysiloxane compounds used in the inventive composition as the component (c), in which the symbol G denotes a tetramethyl guanidyl group of the formula $(Me_2N-)_2C=N-$, Me is a methyl group and Pr is a propyl group:

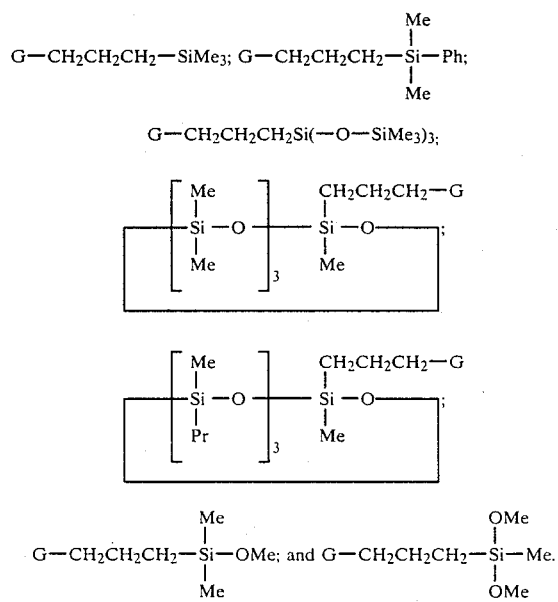

The amount of the component (c) in the inventive composition should be in the range from 0.01 to 5 parts by weight or, preferably, from 0.1 to 2 parts by weight per 100 parts by weight of the diorganopolysiloxane as the component (a). This is because no decreasing effect can be achieved in the time for the formation of a tack-free surface film on the surface of the composition exposed to the atmospheric air when the amount of this component (c) is too small in addition to the poor curability of the composition in the depth of a thick layer at a distance from the surface while an excessively large amount of the component (c) is undesirable due to the possible coloration of the cured composition by heating as an effect of the guanidyl groups.

The guanidyl-containing organosilane or organopolysiloxane compound as the component (c) can readily be obtained by the reaction of guanidine or a derivative thereof with an organosilane or organopolysiloxane having a halogen-substituted alkyl group in the presence of an acid acceptor.

The essential ingredients in the inventive composition are the above described components (a), (b) and (c) and the inventive composition can be prepared by merely blending these three components uniformly. Of course, the inventive composition may optionally contain several known additives conventionally used in the room temperature curable silicone rubber compositions. For example, fillers may be added to the composition as exemplified by siliceous fillers such as finely pulverized quartz, pulverized fused quartz glass, silica aerogel, precipitated silica and diatomaceous earth, metal oxides such as oxides of iron, zinc oxide and titanium dioxide with or without surface treatment with a silane compound, metal carbonates such as calcium carbonate, magnesium carbonate and zinc carbonate, asbestos, glass wools, carbon black, mica powder, and fine powders of synthetic resins such as polystyrene, polyvinyl chloride and polypropylene. The amount of the filler, if added, should be 400 parts by weight or, preferably, 200 parts by weight or less per 100 parts by weight of the diorganopolysiloxane as the component (a). The filler should preferably be dried before blending with the other components to remove any moisture content.

Other optional additives which may be contained in the inventive composition include coloring agents, e.g. pigments and dyes, thixotropy improvers, aging retarders, antioxidants, antistatic agents, flame retardants, e.g. antimony oxide, chlorinated paraffin and the like, and heat conductivity improvers, e.g. boron nitride, diorganopolysiloxanes having no silanolic hydroxy groups, so-called carbon-functional silanes having amino, epoxy, thionyl and the like functional groups, metal salts of carboxylic acids and metal alcoholates in limited amounts.

The above described room temperature curable silicone rubber composition of the present invention comprising essentially the components (a), (b) and (c) and optionally fillers and other additives, while it is storable with stability for a long period of time under a hermetically sealed condition, can readily be cured when exposed to a moisture-containing atmosphere into a rubbery elastomer with good adhesion to the surface of the substrate of, in particular, metal on which it has been cured. No noxious products are formed by the curing of the inventive composition so that corrosion or rust formation never occurs on the surface of a metallic substrate. Furthermore, curing of the inventive composition can proceed uniformly even to a depth of a thick layer without delay and the cured elastomer of the composition exhibits large elongation. By virtue of these advantageous characteristics, the inventive composition can find wide applications as a sealant, caulking material, adhesive agent, coating agent and the like. Since the inventive composition can be diluted, according to need, with an organic solvent, e.g. toluene, xylene and petroleum solvents, ethers, ketones and esters, the composition can be used also as a water repellent agent, fabric treating agent, mold release agent and the like in the form of an organic solution.

In the following, examples of the present invention are given beginning with the preparation of the alkenyloxy-containing cyclic polysiloxanes as the component (b). In the following examples, "parts" always refers to "parts by weight" and the symbols of Me, Pr and G denote a methyl group, a propyl group and a tetramethyl guanidyl group, respectively. The values of the viscosity given for the components in the examples were all measured at 25° C.

EXAMPLE 1

Into a reaction vessel were taken 240 g (1 mole) of 1,3,-5,7-tetramethyl cyclotetrasiloxane and 240 g of tetrahydrofuran as a solvent and 2.5 g of diethyl hydroxylamine as a catalyst were added dropwise to the reaction mixture kept at 15 to 20° C. Thereafter, 162 g (1.8 moles) of trimethyl silanol kept at about the same temperature as above were added dropwise into the reaction mixture over a period of 4 to 5 hours to effect the dehydrogenation reaction. After completion of the reaction, the reaction mixture was distilled to isolate the cyclic polysiloxanes expressed by the formulas (xiii) and (xiv) given before, i.e. tetramethyl di(trimethylsiloxy) cyclotetrasiloxane and tetramethyl trimethylsiloxy cyclotetrasiloxane, respectively.

Into a reaction mixture formed of 416 g (1 mole) of the above obtained tetramethyl di(trimethylsiloxy) cyclotetrasiloxane and 416 g of carbon tetrachloride kept at a temperature not to exceed 30° C. by externally cooling with ice were blown 2 moles of chlorine gas over a period of about 3 hours at a rate of 250 ml per minute to effect the dehydrochlorination reaction. In this case, the chlorine gas was accompanied by a small volume of dry air which served as a catalyst for the dehydrochlorination reaction. After completion of the reaction, carbon tetrachloride was removed from the reaction mixture by distillation to leave the chlorine-containing cyclic polysiloxane expressed by the formula (xv) given before, i.e. tetramethyl dichloro di(trimethylsiloxy) cyclotetrasiloxane, which was a clear, colorless liquid. The yeild was 450 g corresponding to about 93% of the calculated value.

Separately, 3 moles of chorine gas were blown into a mixture composed of 328 g (1 mole) of the tetramethyl trimethylsiloxy cyclotetrasiloxane and 328 g of carbon tetrachloride over a period of about 5 hours to effect the dehyrochlorination reaction. Distallation of the reaction mixture after completion of the reaction gave the chlorine-containing cyclic polysiloxane of the formula (xvi), i.e. tetramethyl trichloro trimethylsiloxy cyclotetrasiloxane, in a yield of about 95% based on the calculated amount.

A reaction mixture was prepared in a reaction vessel with 1566 g (27 moles) of acetone, 313 g of dimethyl formamide corresponding to 20% by weight of the acetone, 263 g (2.6 moles) of triethyl amine and 2 g of copper (I) chloride and, after agitation for 10 minutes, 32.7 g (0.3 mole) of trimethyl chlorosilane were added dropwise into the reaction mixture which served as a dehydrating agent. The temperature of the reaction mixture was increased to 50° to 55° C. and 484 g (1 mole) of the above prepared tetramethyl dichloro di(trimethylsiloxy) cyclotetrasiloxane were added dropwise into the reaction mixture and the reaction was continued for 8 hours under reflux at a temperature of about 60° C.

After completion of the reaction, the precipitates of the hydrochloride of triethyl amine were removed from the reaction mixture by filtration and the filtrate was, after stripping of the acetone and triethyl amine at 60° C. under a reduced pressure of 50 mmHg, subjected to rectifying distillation under reduced pressure to give 380 g of a clear, colorless liquid product at 109° C. of the column top temperature under a pressure of 2 mmHg. This liquid product was identified to be the desired cyclic tetrasiloxane of the formula (i) in which the group X was an isopropenyloxy group from the results of the analyses given below. The yield was about 72% of the calculated value.

| Elementary analysis: | C | H | Si |
| --- | --- | --- | --- |
| Calculated, % | 36.3 | 7.6 | 31.9 |
| Found, % | 36.5 | 7.7 | 31.6 |

Molecular weight: 528 by the gas mass spectrometry
Refractive index $n_D^{25}$: 1.4158
Density $d_4^{25}$: 0.9947
Infrared absorption spectrum: see FIG. 1

Similarly to the above procedure, a reaction mixture was prepared in a reaction vessel with 1566 g (27 moles) of acetone, 313 g of dimethyl formamide corresponding to 20% by weight of the acetone, 394 g (3.9 moles) of triethyl amine and 2 g of copper (I) chloride and, after agitation for 10 minutes, 32.7 g (0.3 mole) of trimethyl chlorosilane were added thereto which served as a dehydrating agent. The temperature of the reaction mixture was increased to 50° to 55° C. and 430 g (1 mole) of the above prepared tetramethyl trichloro trimethylsiloxy cyclotetrasiloxane were added dropwise into the reaction mixture to carry out the reaction for 8 hours under reflux at a temperature of about 60° C.

After completion of the reaction, the reaction mixture was treated in substantially the same manner as in the preceding case and the rectifying distillation of the filtrate after removal of the triethyl amine hydrochloride and stripping of acetone and triethyl amine at 60° C. under a pressure of 50 mmHg gave 332 g of a clear, colorless liquid product at 105° C. of the column top temperature under a pressure of 2 mmHg. This liquid product was identified to be the desired cyclic tetrasiloxane of the formula (vii) in which the group X was an isopropenyloxy group from the results of the analyses given below. The yeild was about 67% of the calculated value.

| Elementary analysis: | C | H | Si |
| --- | --- | --- | --- |
| Calculated, % | 38.7 | 7.3 | 28.3 |
| Found, % | 38.3 | 7.4 | 28.1 |

Figure 2:
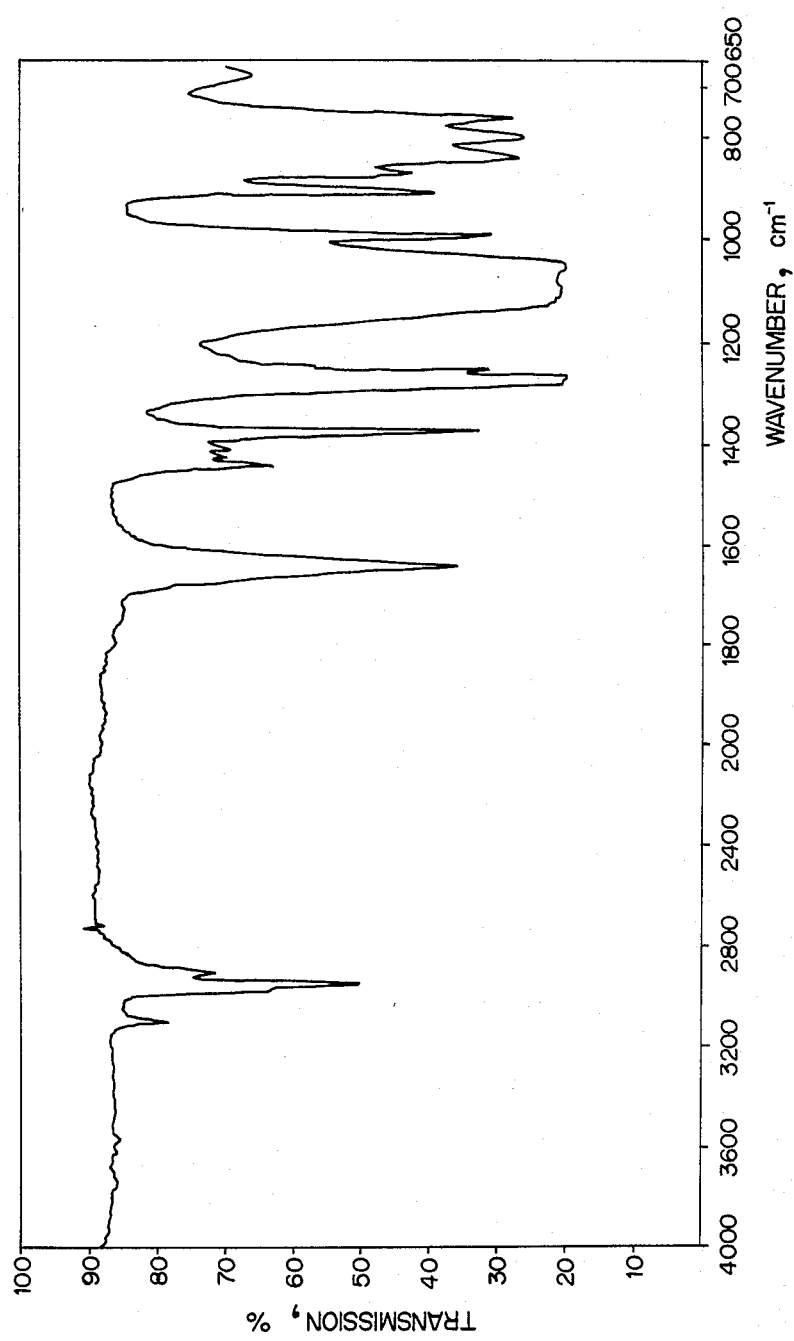

Molecular weight: 496 by the gas mass spectrometry
Refractive index $n_D^{25}$: 1.4178
Density $d_4^{25}$: 0.9994
Infrared absorption spectrum: see FIG. 2

EXAMPLE 2

A base compound was prepared by blending 60 parts of a dimethylpolysiloxane having a viscosity of 5200 centistokes and terminated at both molecular chain ends with silanolic hydroxy groups and 40 parts of calcium carbonate filler treated with a fatty acid on the surface and uniformizing the mixture by passing once through a three-roller mill.

The above prepared base compound was further admixed with 1.8 parts of the cyclic tetrasiloxane of the formula (i) in which the group X was an isopropenyloxy group (which is referred to as the siloxane B-1 hereinbelow), 2.0 parts of the cyclic tetrasiloxane of the formula (vii) in which the group X was an isopropenyloxy group (which is referred to as the siloxane B-2 hereinbelow) and 0.5 part of a guanidyl-containing silane 1-tetramethylguanidyl 3-trimethylsilyl propane (which is referred to as the compound C-1 hereinbelow) into a uniform composition.

The above prepared composition was shaped into a sheet of 2 mm thickness and the sheet was kept standing for 7 days in an atmosphere of 55% relative humidity at 20° C. to be converted into a rubbery elastomer sheet. Curing of the composition was uniform and complete throughout the thickness of the sheet.

The mechanical properties of the thus obtained cured rubber sheet were measured as cured in the above and after aging for 5 days at 150° C. to give the results shown in Table 1 below. In this table, the values of the hardness were obtained by the procedure specified in JIS K 6301 and the values of the tensile strength, ultimate elongation and adhesive strength were obtained according to the procedures specified in JIS A 5758.

TABLE 1

| Example No. | | 2 | 3 | 4 | 5 | 6 | 7 | 8 |
|---|---|---|---|---|---|---|---|---|
| Hardness (JIS) | As cured | 12 | 14 | 24 | 20 | 15 | 11 | 12 |
| | After aging | 14 | 17 | 28 | 23 | 17 | 13 | 13 |
| Tensile strength, kg/cm$^2$ | As cured | 14 | 16 | 12 | 12 | 16 | 12 | 16 |
| | After aging | 13 | 15 | 14 | 12 | 15 | 12 | 16 |
| Ultimate elongation, % | As cured | 1190 | 1070 | 350 | 420 | 380 | 1280 | 1040 |
| | After aging | 1030 | 980 | 310 | 370 | 350 | 1150 | 910 |
| Adhesive strength, minimum, kg/cm$^2$ | As cured | 4.8 | 5.1 | 5.6 | 4.8 | 5.2 | 4.3 | 4.4 |
| | After aging | 4.9 | 5.0 | 5.6 | 4.5 | 5.0 | 4.5 | 4.3 |

Further, the performance of the above prepared composition as a caulking material was examined by filling a gap space of 25 cm long and 2 cm × 1 cm cross section formed by two plates of marble stone having dimensions of 25 cm square and 2 cm thickness placed flatly side by side 1 cm apart from each other to be cured in situ by the exposure to the atmospheric air. In the course of curing of the composition, the phenomenon of so-called blistering, due to the air bubbles entrained in the composition by mixing in the preparation thereof appearing on the surface along with the shrinkage of the composition by curing was not observed.

Then, the above prepared test piece of the marble stone plates caulked with the composition was subjected to weathering test by exposing to open air as held at 45° inclination under the following conditions to find that no stain was noted on the surface of the marble stone plates for which the composition as the caulking material was responsible. The irradiation dose of sunlight energy is a value for a horizontal surface.

Duration of exposure: 120 days
Total rainfall: 133 mm
Number of rainfalls: 26 times
Irradiation dose of sun light energy: 34501 Cal/cm$^2$
 Dose of ultraviolet light (300–400 nm); 2833 Cal/cm$^2$
 Dose of visible light (400–700 nm); 16907 Cal/cm$^2$
 Dose of infrared light (700–1200 nm); 14761 Cal/cm$^2$

EXAMPLE 3

A base compound was prepared by uniformly blending 60 parts of a dimethylpolysiloxane having a viscosity of 5200 centistokes and terminated at both molecular chain ends with silanolic hydroxy groups and 40 parts of a calcium carbonate filler treated on the surface with a fatty acid and dried for 2 hours in a sealed mixing machine in an atmosphere of nitrogen at 110° C. for 30 minutes under an anhydrous condition.

The above prepared base composition was further admixed with 7.2 parts of the siloxane B-1, 0.8 part of the siloxane B-2 and 1 part of the compound C-1 used in Example 2 followed by a defoaming treatment to give a curable composition.

The thus prepared curable composition was storable with stability in a hermetically sealed condition for 6 months or longer without coloring or discoloration at all. After storage for 6 months, the composition was shaped into a sheet-like form of 2 mm thickness and kept standing in an atmosphere of 55% relative humidity at 20° C. for 7 days to be converted into a cured rubber sheet by the reaction with the atmospheric moisture. The mechanical properties of this cured rubbery sheet were measured as cured and after aging for 5 days at 150° C. to give the results shown in Table 1.

The composition was further taken to fill a glass dish of 12 mm depth and kept standing in an atmosphere of 55% relative humidity at 25° C. to examine the curing velocity, corrosiveness by the testing method specified in MIL A-46146 and adhesive strength by the testing method specified in JIS A 6758. The results were that the curing velocity was 2 to 3 mm per day, no corrosivenes was found and very firm adhesion was obtained to the surfaces of glass, aluminum, copper, epoxy resin and ABS resin.

EXAMPLE 4

A curable composition was prepared by admixing 100 parts of the base compound prepared in Example 2 with 2 parts of the siloxane B-2 and 1 part of the compound C-1 and the composition was shaped into a sheet-like form of 2 mm thickness which was kept standing for 7 days in an atmosphere of 55% relative humidity at 20° C. to be converted into a cured rubber sheet. Curing was uniform and complete throughout the thickness of the sheet. The mechanical properties of the cured rubber sheet were measured as cured and after aging for 5 days at 150° C. to give the results shown in Table 1.

EXAMPLE 5

A base compound was prepared by uniformly blending 60 parts of a dimethylpolysiloxane having a viscosity of 20,600 centistokes and terminated at both molecular chain ends with silanolic hydroxy groups and 40 parts of a calcium carbonate filler treated on the surface with a fatty acid and dried for 2 hours in an atmosphere of nitrogen gas at 110° C. under an anhydrous condition in a sealed blending machine for 30 minutes.

The above prepared base compound was further admixed with 8 parts of the siloxane B-2 and 1 part of the compound C-1 used in Example 2 also under an anhydrous condition followed by defoaming treatment to give a curable composition, which was shaped into a sheet-like form of 2 mm thickness and kept for 7 days in an atmosphere of 55% relative humidity at 20° C. to be converted into a cured rubber sheet. The mechanical properties of this cured rubber sheet were measured as cured and after aging for 5 days at 150° C. to give the results shown in Table 1.

The curable composition was also subjected to the tests of the curing velocity, corrosiveness and adhesive strength in the same manner as in Example 3 to give the results as satisfactory as in Example 3.

EXAMPLE 6

A base compound was prepared in substantially the same manner as in the preceding example by uniformly blending 88 parts of the same diorganopolysiloxane as used in the preceding example and 12 parts of a fumed silica filler having a specific surface area of 170 m²/g and treated on the surface with hexamethyl disilazane. This base compound was further admixed with 8 parts of the siloxane B-2 and 1 part of the compound C-1 to give a curable composition.

The mechanical properties of the cured rubber sheet obtained by curing the above prepared curable composition in substantially the same manner as in the preceding example were as shown in Table 1.

EXAMPLE 7

A base compound was prepared by blending 60 parts of a dimethylpolysiloxane having a viscosity of 5870 centistokes and terminated at both molecular chain ends with silanolic hydroxy groups and 40 parts of a calcium carbonate filler, which was uniformized by passing once through a three-roller mill.

The above prepared base compound was further admixed with 1.8 parts of an isopropenyloxy-containing cyclic tetrasiloxane, which is referred to as the siloxane B-3 hereinbelow, expressed by the structural formula

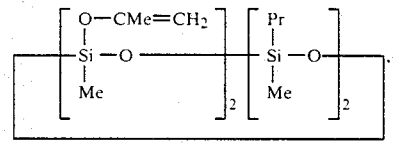

0.2 part of another isopropenyloxy-containing cyclic tetrasiloxane, which is referred to as the siloxane B-4 hereinbelow, expressed by the structural formula

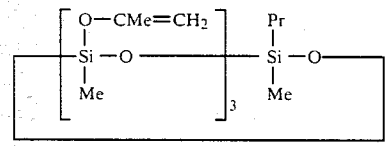

and 0.5 part of the compound C-1 used in Example 2 to give a curable composition.

The thus obtained curable composition was shaped into a sheet-like form of 2 mm thickness and kept standing for 7 days in an atmosphere of 55% relative humidity at 20° C. to be converted into a cured rubber sheet of which the mechanical properties were measured as cured and after aging for 5 days at 150° C. to give the results shown in Table 1.

The composition was also subjected to the outdoor exposure test with two marble stone plates in the same manner as in Example 2 to give quite satisfactory results in respect of the surface stain.

EXAMPLE 8

A curable composition was prepared by blending 100 parts of the base compound prepared in Example 3, 7.2 parts of the siloxane B-1 used in Example 2, 0.8 part of the siloxane B-4 used in Example 7 and 1 part of a guanidyl-containing siloxane compound 3-tetramethyl-guanidylpropyl tris(trimethylsiloxy) silane of the formula G—CH$_2$CH$_2$CH$_2$Si(OSiMe$_3$)$_3$ followed by defoaming treatment. This composition was storable in a hermetically sealed condition with stability over a period of 6 months or longer without coloring or discoloration at all.

After storage for 6 months, the composition was shaped into a sheet-like form of 2 mm thickness which was kept standing for 7 days in an atmosphere of 55% relative humidity at 20° C. to be converted into a cured rubber sheet, of which the mechanical properties were measured as cured and after aging for 5 days at 150° C. to give the results shown in Table 1.

What is claimed is:

1. An organocyclopolysiloxane represented by the general formula

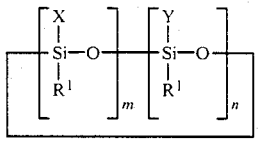

in which
X is an alkenyloxy group of the formula —OCR$^3$=CH—R$^2$,
Y is a trimethylsiloxy group of the formula —O—Si(CH$_3$)$_3$,
R$^1$ is monovalent hydrocarbon group having from 1 to 8 carbon atoms,
R$^2$ and R$^3$ are each independently a hydrogen atom or a substituted or unsubstituted monovalent hydrocarbon group having from 1 to 6 carbon atoms,
m is 2 or 3, and
n is a positive integer with the proviso that m+n is equal to 4.

2. The organocyclopolysiloxane as claimed in claim 1 wherein the group denoted by X is an isopropenyloxy group of the formula —O—C(CH$_3$)=CH$_2$.

3. A room temperature curable organopolysiloxane composition which comprises:
(a) 100 parts by weight of a diorganopolysiloxane terminated at both molecular chain ends with silanolic hydroxy groups;
(b) from 0.01 to 25 parts by weight of an organocyclopolysiloxane represented by the general formula

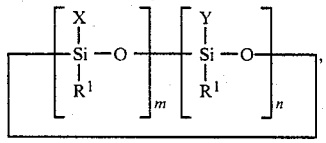

in which X is an alkenyloxy group of the formula —OCR$^3$=CH—R$^2$, Y is a trihydrocarbylsiloxy group of the formula —O—SiR$^1_3$ or a monovalent hydrocarbon group having from 1 to 5 carbon atoms, R$^1$ is a monovalent hydrocarbon group having from 1 to 8 carbon atoms, R$^2$ and R$^3$ are each independently a hydrogen atom or a substituted or unsubstituted monovalent hydrocarbon group having from 1 to 6 carbon atoms, m is a positive integer of 2, 3 or 4 and n is zero or a positive integer with the proviso that m+n is equal to 4, 5 or 6; and
(c) from 0.01 to 5 parts by weight of a guanidyl-containing organosilicon compound having, in a molecule, at least one substituted or unsubstituted guanidyl group represented by the general formula ($R^4_2N-$)$_2C=N-$, in which each $R^4$ is a hydrogen atom or a monovalent hydrocarbon group independently from the others.

4. The room temperature curable organopolysiloxane composition as claimed in claim 3 wherein the diorganopolysiloxane as the component (a) is a dimethylpolysiloxane.

5. The room temperature curable organopolysiloxane composition as claimed in claim 4 wherein the dimethylpolysiloxane has a viscosity of at least 25 centistokes at 25° C.

6. The room temperature curable organopolysiloxane composition as claimed in claim 3 wherein the group denoted by X in the general formula of the component (b) is an isopropenyloxy group of the formula $-O-C(CH_3)=CH_2$.

7. The room temperature curable organopolysiloxane composition as claimed in claim 3 wherein m is 2 or 3 and m+n is equal to 4.

8. The room temperature curable organopolysiloxane composition as claimed in claim 3 wherein the trihydrocarbylsiloxy group denoted by Y is a trimethylsiloxy group of the formula $-O-Si(CH_3)_3$.

9. The room temperature curable organopolysiloxane composition as claimed in claim 3 wherein the monovalent hydrocarbon group denoted by Y is a methyl group or a propyl group.

10. The room temperature curable organopolysiloxane composition as claimed in claim 3 wherein the component (b) is a mixture of a first organocyclopolysiloxane of the general formula in which m is 2 and n is 2 or 3 and a second organocyclopolysiloxane of the general formula in which m is 3 or 4.

11. The room temperature curable organopolysiloxane composition as claimed in claim 10 wherein the molar ratio of the first organocyclopolysiloxane to the second organocyclopolysiloxane is in the range from 99.5:0.5 to 70:30.

12. The room temperature curable organopolysiloxane composition as claimed in claim 3 wherein the guanidyl group in the component (c) is a tetramethylguanidyl group of the formula

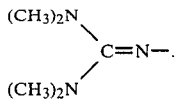

13. The room temperature curable organopolysiloxane composition as claimed in claim 3 wherein the component (c) is 1-tetramethylguanidyl 3-trimethylsilyl propane.

14. The room temperature curable organopolysiloxane composition as claimed in claim 3 wherein the component (c) is 3-tetramethylguanidylpropyl tris(trimethylsiloxy) silane.

15. The room temperature curable organopolysiloxane composition as claimed in claim 3 wherein the amount of the component (b) is in the range from 0.1 to 20 parts by weight per 100 parts by weight of the component (a).

16. The room temperature curable organopolysiloxane composition as claimed in claim 3 wherein the amount of the component (c) is in the range from 0.1 to 2 parts by weight per 100 parts by weight of the component (a).

17. The room temperature curable organopolysiloxane composition as claimed in claim 3 which further comprises a filler in an amount of 400 parts by weight or smaller per 100 parts by weight of the component (a).

* * * * *